United States Patent [19]
Wright et al.

[11] Patent Number: 5,579,107
[45] Date of Patent: Nov. 26, 1996

[54] METHOD AND APPARATUS FOR DRY PARTICLE ANALYSIS

[75] Inventors: Craig Wright; Curt Torgerson, both of San Diego, Calif.

[73] Assignee: Horiba Instruments, Inc., Irvine, Calif.

[21] Appl. No.: 451,023

[22] Filed: May 25, 1995

[51] Int. Cl.⁶ .......................... G01N 15/02; G01N 21/85
[52] U.S. Cl. ........................ 356/336; 73/865.5; 241/39; 356/440
[58] Field of Search ........................ 356/335, 336, 356/338, 339, 438, 440; 73/865.5, 24.03.24.06, 864.81; 241/39

[56] References Cited

U.S. PATENT DOCUMENTS

| | | | |
|---|---|---|---|
| 3,219,281 | 11/1965 | Jasper et al. | 241/5 |
| 3,269,189 | 8/1966 | Monk | 73/432 |
| 3,328,587 | 6/1967 | Brown et al. | 250/218 |
| 4,047,814 | 9/1977 | Westcptt | 356/38 |
| 4,391,411 | 7/1983 | Colburn | 241/1 |
| 4,515,274 | 5/1985 | Hollinger et al. | 209/3.1 |
| 4,563,581 | 1/1986 | Perten | 250/338 |
| 4,708,485 | 11/1987 | Illy | 356/440 |
| 4,860,959 | 8/1989 | Handleman | 241/39 |
| 4,875,629 | 10/1989 | Brors | 241/39 |
| 4,895,034 | 1/1990 | Poole | 73/865 |
| 5,035,364 | 7/1991 | Escallon | 241/5 |
| 5,359,907 | 11/1994 | Baker et al. | 73/865.5 |

FOREIGN PATENT DOCUMENTS 0144018  6/1995  European Pat. Off. .

OTHER PUBLICATIONS 1987 brochure entitled "New Microtrac II"; Leeds & Northrup. (no month).

*Primary Examiner*—Richard A. Rosenberger
*Attorney, Agent, or Firm*—Poms, Smith, Lande & Rose

[57] ABSTRACT

A dry particle analyzer includes a vibrating sieve cup drizzling particles downwardly with first, second, and third sheath air flows being provided to separate the particles from boundary walls and to form the drizzling particles into a columnated flow for optical analysis. The particles drop vertically as a drizzle with gravitational assistance from a bulk sample to an analysis chamber. Along the way to the analysis chamber, the particles are subjected to an interval of high air flow shear, and to high turbulence of the air flow to break up agglomerations of particles.

22 Claims, 4 Drawing Sheets

METHOD AND APPARATUS FOR DRY PARTICLE ANALYSIS

CROSS REFERENCE TO RELATED APPLICATION

The subject matter of the present application is related to subject matter set forth in an earlier application Ser. No. 07/975,019, filed Nov. 12, 1992, now U.S. Pat. No. 5,359,907, issued Nov. 1, 1994 and also assigned to the same assignee as is the present application. The subject matter of this earlier application is hereby specifically incorporated herein as though it were fully set out.

BACKGROUND OF THE INVENTION

Field of the Invention

The present invention relates to particle analysis. More particularly, the present invention relates to methods and apparatus for analysis by optical means of a physical characteristic, such as particle size distribution, of a bulk sample of particulate material. Analysis of the physical characteristic is accomplished by entraining the dry particulates as a drizzle in ambient air without the use of a conventional liquid particle dispersant, or of liquid stirring devices. The particulates are additionally subjected to the action of turbulent high-velocity air in order to break up agglomerations of particles. The size and number of individual particles in the bulk sample is then assayed optically, and collected data from the assay may be reported as a particle size distribution for the bulk sample.

Related Technology

Wet Analysis Processes

The art of particle analysis includes two broad categories of apparatus. On the one hand, analysis of particulates native in liquid (pigments of paint in a carrier liquid, for example) has lead to the development of "wet process" particle analyzers which use various techniques to determine certain characteristics of the particulates in liquid suspension. Illustrative of this type of analyzer is that described in U.S. Pat. No. 4,047,814, to V. Westcott wherein particulates suspended in a liquid are caused to "plate out" on a substrate by application of a force field. The force field may be magnetic or electrostatic, for example. Analysis of the particulates is accomplished after fixing them on the substrate and drying preparatory to optical (microscopic) inspection. An illustrative example of the use of the Westcott invention is directed to analysis of metallic wear particles in lubricating oil from an engine.

An alternative technology, that of electromagnetic radiation (i.e., light) obscuration, scattering and diffraction analysis, allows particulates to be analyzed in their native liquid without the need of fixing and drying as required by Westcott. With this technology, a liquid sample with particulates therein is illuminated in an analysis cell with selected light or other radiation. Analysis of the resulting forward or back light scattering, diffraction, or obscuration provides the desired indication of the size distribution of the particulates in the sample.

Of course, some particulates tend to settle out of the liquid, so that stirring devices for the liquids and particulates therein have had to be developed. However, the stirring devices themselves can present dead spaces within which particulates may be trapped. Typical of this category of particle analysis devices is one by Leeds and Northrop, a unit of General Signal, Inc. For example, a particle analyzer from this company is known under the name "Microtrac II" and is depicted and described in a 1987 brochure. This analyzer includes as a stirring device a so-call, "particle circulator", which recirculates liquid with particulates therein through an analysis cell. Almost in defense of this stirring device, the particle circulator itself is stated to be free of dead spaces in which particulates could collect or settle out. Also, a common problem with this type of wet process analysis with stirring is stated to be air entrainment in which bubbles are created in the carrier liquid and can interfere with the measurement. The particle circulator of the Microtrac II also assertedly solves to some extent the problem of air entrainment in the carrier liquid. Thus, it is seen that the wet process analysis of particulates has its own set of problems, and that a solution to one problem may itself impose its own deficiencies on the art.

The foregoing type of wet process particle analyzer is also applied to measurement of particulates not native to liquid by dispersing the particulates in a dispersant liquid. Of course, this expedient raises the questions of compatibility of the particulates with the dispersant liquid. Questions of, for example, wetting the particulates with the liquid, of solution of particulates or constituents thereof in the dispersant, and of agglomeration of the particulates in the liquid, to name just a few are concerns with this type of analysis. However, the degree to which the problems of wet particulate analyzers are brought to the measurement of originally dry particulates, and the degree to which these problems are solved, or remain unsolved, is the subject of on going debate in the art.

Another "wet process" particle analyzer is seen in U.S. Pat. No. 4,515,274, issued 7 May 1985 to J. D. Hollinger, et al., and assigned to Coulter Corporation. According to the teaching of the '274 patent, particles in a liquid suspension media may be passed through an analysis cell for counting and characterization. A flow of sheath liquid is used to centralize the particles as they pass through an illuminator of the analysis cell. The problem of de-agglomerating the particulates does not appear to be addressed by the '274 patent.

U.S. Pat. No. 4,860,959, issued 29 Aug. 1989 to A. R. Handleman, and assigned to Semi-Bulk Systems, Inc., is believed to disclose a device for subjecting particles dispersed in a fluid to a shearing action for the purpose of de-agglomerating the particles. The particles are disclosed to be aggregations of crystals and immiscible liquids, for example, dispersed, slurried, or emulsified in a liquid. Paints and food products are set out as examples of the types of liquid products which may benefit from de-agglomeration of the particles by shearing. The '959 patent is not believed to address the de-agglomeration of particulates in a dry condition.

Dry Analysis Processes

In view of the above, dry analysis of dry particulates, and the subsequent complete avoidance of the problems associated with the "wet process" particle analyzers, seems a desirable goal. Thus, many have labored to develop the other major category of particle analysis device, the dry process analyzer. For example, U.S. Pat. No. 3,269,189, of W. G. Monk, is believed to teach a device for classifying particulates by size and weight in a vacuum chamber by use of vibration and a controlled air or gas flow. At about the same time, the application of optical techniques to dry particle analysis was taught by U.S. Pat. No. 3,328,587, of T. J. A. Brown, et. al. The device of Brown maintains the particulate sample in a state of consolidation, and appears to rely for its operation only on back scatter of incident light from the sample. U.S. Pat. No. 4,563,581, of Perten discloses a later effort directed to an analyzer in which the particulate sample is also compacted in an analysis cell and back scatter alone apparently provides the available information about the sample.

U.S. Pat. No. 4,895,034, to Poole, is directed to an entirely different method of particle size analysis, that of aerodynamic and optical "time of flight" analysis. According to this teaching, particles are impelled in a cloud through a nozzle, and their size is optically measured by transit time across a known distance. Poole teaches to disburse particles as a cloud in a carrier stream of air using an air blast and agitation.

Poole apparently teaches to separate particles from the bulk sample by directing a stream of pressurized gas at the sample. The resulting particulate "cloud" is subjected to a shearing action at an annular orifice defined cooperatively by a seat and a tapered needle-like pin. In principle, the de-agglomerating methodologies adapted by Handleman and Poole are the same, one working in liquid and the other in gas. However, experience has shown that the lower viscosity of gas (and resulting lower shear force applied to small particulates) results in less than satisfactory operation for de-agglomerating particulates in gas with the apparatus taught by the Poole '034 patent.

An effort directed to the analysis of particulates disbursed in a flow of air, which allows back scatter, as well as forward scatter or diffraction and obscuration techniques to be employed, is represented by the European patent application, publication number 0 144 018, having a publication date of 12 Jun. 1985. This latter effort provides an observation chamber which prepares a particulate sample in an air stream for optical analysis. The observation chamber itself relies, however, on an inflow of particulates, such as coal dust, already conveyed in an air stream. A "shower head" type of pressurized air ejector is employed to entrain additional ambient air, in addition to mixing compressed air with the particulate sample and its original conveying gas flow. How the particles are introduced from a bulk sample into the conveying gas stream is not detailed in this publication.

A persistent problem with dry particle analyzers is the feeding of particulates from a bulk into a gas stream for analysis. That is, many particulates simply by their nature tend to aggregate, clump, or agglomerate. The particles may contain absorbed moisture, for example, or may be resinous. Moisture or resin in the agglomerations of particles will cause the agglomerations to stick together, so that individual particle size can not be accurately measured. Alternatively, the particles may adhere to one another because of electrostatic charge. Regardless of the reason why particular particles tend toward clumping, it is apparent that characteristics like particle size distribution cannot be accurately measured when the particles clump together. Also, the smaller the particles are, the more difficult it becomes to break up agglomerations of the particles. The difficulty of this de-agglomeration was pointed out above with respect to the Coulter apparatus. Using gas shear principles, smaller particles are more difficult to apply enough shearing force to overcome the agglomeration effects.

De-agglomerators

Accordingly, the art has developed several categories of devices which use various methodologies of operation and which are variously successful in breading up agglomerations of particles. Some of these devices, however, are so violent in their operation that they can fracture the particles in the process of breaking up agglomerations. Consequently, these devices could not be used in a particle size analyzer because it is the particle size distribution of the original sample which is to be measured, not the size distribution after some of the particle have been fractured into smaller particles.

U.S. Pat. No. 4,875,629, issued 24 Oct. 1989 is believed to disclose a particle impact pulverizer in which oppositely-directed high-speed streams of the dry particles carried in air streams are collided head-on with one another. This device may be effective to break up agglomerations of the particles. However, it would also pulverize at least some of the particles in a sample so that an accurate particle size distribution measurement of the sample could not be obtained.

U.S. Pat. No. 3,219,281, issued 23 Nov. 1965 is believed to teach a particle impact pulverizer in which a high-speed stream of particles in a carrier gas (steam) are collided against a bluff surface. This apparatus is directed to providing a particle size of about 75 microns, which is too course for consideration in particle size distribution analysis. Also, this apparatus also shares the possibility of fracturing, or reducing to a smaller size, particles of the original sample. Accordingly, this apparatus is seen as not seen as being desirable for use in de-agglomerating particulates for size distribution analysis.

U.S. Pat. No. 4,391,411, is believed to disclose another method of breaking up particles or agglomerations of particulates. This apparatus essentially uses a pair of sequentially arranged centrifugal blowers or fans which convey a stream of particles in air. The particles are comminuted or pulverized by an assertedly rapid pressure change experienced at a change in cross sectional area of the duct between the two blowers. Undoubtedly, the particles are also broken up by the combined action of mechanical impact with the blades of the centrifugal fans and the assertedly rapid change in pressure within the connecting duct. This device would not be usable for de-agglomerating particulates for size distribution analysis because of the probability that the blower blades would fracture or break at least some of the particles. As explained above, such alteration of the sample would result in a distorted test result for the sample.

Finally, U.S. Pat. No. 5,035,364, issued 30 Jul. 1991, is believed to disclose a de-agglomerator for particulate material which is asserted to operate by subjecting the agglomerations to rapid particle acceleration and turbulent flow with a sufficient residence time to assure de-agglomeration of the particulates and with a minimum of addition of energy to the flow stream of particles. In this device, a cloud of particles in a carrier gas is passed along a divergent primary flow passage having at least one secondary flow path opening thereto at a tangential direction and angularly in the direction of flow along the primary flow path. Assertedly, the primary flow and particulates are subjected to a combination of effects including vortex flow, shear, centripetal forces, and boundary layer drag, all acting in opposition to inertial forces.

With a de-agglomerator according to the '364 patent, it would appear that unless a spinning cloud of particulates is acceptable as a product of the operation of this device, two or more secondary flow paths would have to be used, with these arranged to precisely cancel the angular velocity imposed on the flow in the primary flow path by all of the vortices induced by the secondary flows.

SUMMARY OF THE INVENTION

In view of the deficiencies of the related technology, a primary object for this invention is to overcome one or more of these deficiencies.

An additional object is to provide a particle de-agglomerator which is effective to break up agglomerations of particles down to a size of one micron or smaller.

In view of the above, the present invention provides a dry particle analyzer including means for drizzling particles from a bulk sample thereof, means for providing a downward flow of first sheath ambient air around the drizzling particles in a flow regime of laminar bulk flow with a surrounding viscous boundary layer, means for suddenly changing the flow regime of the drizzling particles and first sheath air to a flow regime with a surrounding second sheath of high velocity air causing high shear and acceleration of the drizzling particles and first sheath air flow and with admixture of the second sheath air, means for columnating and decelerating the particles and the admixture of first sheath air and second sheath air, means for providing a downward and columnar flow of third sheath ambient air around the columnated drizzled particles and first and second air flows admixed together and substantially in velocity union therewith, and means defining a vertically downwardly extending optical analysis cell passage receiving the unified downward flow of drizzled particles and admixed first and second sheath air surrounded by the third sheath air for columnated downward flow therein, whereby the drizzled particles flow downwardly continuously from the bulk sample and through the analysis cell passage.

Further to the above, the present invention provides a dry particle analyzer apparatus including means for providing a cloud of drizzled particles gravitationally descending in a relatively low-velocity laminar bulk flow of surrounding ambient first sheath air with a surrounding low-velocity viscous boundary layer, and a de-agglomerator for affecting attrition of agglomerations of the particulates, the de-agglomerator including a Coanda type aspirator defining an opening through which the bulk flow of drizzled particles and first sheath ambient air is received, the aspirator receiving pressurized air and defining an annular radial gap surrounding the opening and from which a high-velocity second sheath air flow is discharged axially of the opening, thereby to apply a sudden high air flow shear to the particles and first sheath air flow.

Importantly, the present dry particle analyzer method and apparatus conveys the particulates continuously vertically downwardly from their separation out of the bulk particulate sample and through the analysis passage of the cell. The particles flow through and outwardly of the cell with smooth continuous flow.

Further, should any particulates contact the cell walls and adhere thereto, the cell is small and easily cleaned, so that integrity of subsequent tests is not thrown into question. The flow path length from the bulk sample to the analysis passage is short, on the order of only a few inches, and is all vertical with downward flow so that virtually no opportunity exists for particulates to settle out of the conveying air flow. No dead volume exists in the air and particle flow path, which is virtually straight with no twists or bends to cause air flow turbulence and pressure losses prior to the analysis cell.

Still further, the cell design does not fight gravity, so that gravitational force is an assistance rather than a hindrance to delivery of the particulates into the analysis passage of the test cell.

Additionally, because of the small overall size of the analysis cell, it may be employed within the test well of a conventional particle analyzer previously used for liquid-borne samples. A vibratory sifter cup and vibration drive therefor can easily be stacked above the test well of the conventional particle analyzer so that no additional bench-top space is required. Because the outlet port of the analysis cell is disposed at the top of the ascending leg of a J-shaped flow path for the analysis cell, connection of the analysis cell to an external vacuum source is simplified. In fact, the vacuum source plumbing can exit out the top of the test well opening of the conventional particle analyzer with no need for extensive changes to the latter.

Still further, the particle analyzer includes a de-agglomerator which is effective to break up agglomerations or aggregations of particulates down to a particle size of less than one micron, substantially without fracturing the particulates, so that a particle size distribution of a sample may be accurately obtained. This de-agglomerator also assists in moving a cloud of particulates from the sifter for the bulk sample through the analysis cell and to the vacuum source so that accumulation of particulates within the analysis cell is avoided. This de-agglomerator is believed to function by creating an annular sonic flow of pressurized air, and introducing this sonic flow of air to and around the downwardly flowing particulate cloud.

Consequently, the particulate cloud experiences a sudden change in flow regime from one in which the viscous boundary layer of the cloud is at a slow or nearly zero speed adjacent to the walls of the flow path, to one in which a surrounding sheath of air is of high velocity, and possibly near sonic in velocity. In fact, under some conditions of operation, the surrounding sheath of high velocity air may be of sonic velocity and be under expanded by its passage through a convergent nozzle. Consequently, the under-expanded sonic air flow with further expand with attendant formation possibly of localized oblique shock waves in the air flow as the air expands to pressure equilibrium with the local pressure condition. The particulates in the flowing cloud are believed to be subjected to an interval of very high shear and turbulent flow conditions as the sonic air flow circumscribing the particulate cloud diffuses to a lower velocity and admixes with the air of the particulate cloud itself. A feature of the de-agglomerator flow path insures that after a short interval of high shear, additional turbulence is added to the flow regime experienced by the particulates.

The de-agglomerator flow path itself is shaped to form a shallow divergent nozzle so that diffusion of the sonic air along with the cloud of particulates provides an essentially columnated flow of de-agglomerated particulates in air issuing from an outlet of the de-agglomerator into the analysis cell. A provision is made to provide a surrounding flow of ambient sheath air also passing into the analysis cell at substantially the same pressure and velocity along with the columnar flow of de-agglomerated particles. Consequently, the columnar flow of de-agglomerated particles passes though the analysis cell with little or no diffusion as a nearly perfect columnar particulate cloud of de-agglomerated particulates.

The above, and additional advantages of the present invention will be appreciated from a reading of the following detailed description of a single preferred embodiment of the invention, taken in conjunction with the appended drawing Figures, which are briefly described immediately below:

BRIEF DESCRIPTION OF THE DRAWING FIGURES

FIG. 1 provides a perspective view of a particle analyzer embodying the invention;

FIG. 2 is a fragmentary elevation view, partially in cross section taken at line 2—2 of FIG. 1 and illustrating a portion of the particle analyzer seen in this earlier Figure;

FIG. 3 is a cross sectional view of a portion of the apparatus seen in FIG. 2 taken along line 3—3 of this Figure;

FIG. 4 provides a greatly enlarged fragmentary cross sectional view of a portion of FIG. 3; and FIGS. 5, 6 and 7 provide an exploded perspective view of a portion of the apparatus embodying the present invention.

DETAILED DESCRIPTION OF A PREFERRED EMBODIMENT OF THE INVENTION

Figure 1:
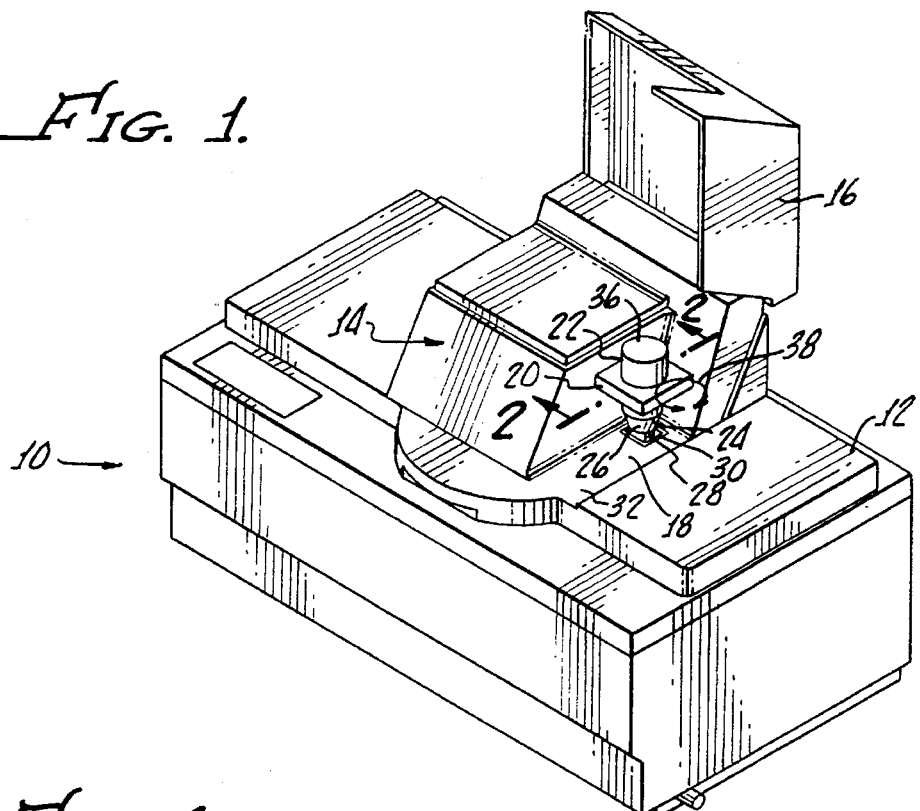

Viewing FIG. 1, a particle analyzer 10 includes a housing 12 which may sit upon a bench top (not shown). The particle analyzer 10 includes a dry particle feeder 14 which is stacked upon the remainder of the analyzer 10, and which has a cover portion 16, shown in an open position. The open cover 16 reveals a sample chamber 18 of the dry particle feeder 14 wherein is disposed a vibratory sieve cup clamp 20 holding a sample sieve cup 22. Sample sieve cup 22 includes a funnel-like lower portion 24 extending downwardly into the open upper end or mouth 26 of a conduit member 28 (viewing also FIG. 2). The conduit member 28 extends upwardly through an opening 30 defined by a cover plate portion 32 of the dry particle feeder 14. Cover plate 32 spans across an analysis cell well (not seen in FIG. 1, but referenced generally with numeral 34 in FIG. 2). The sample sieve cup 22 includes an open cylindrical portion 36 into which a powdered, or granular, or otherwise particulate sample (identified further below) may be placed for particle size analysis using the analyzer 10.

Figure 2:
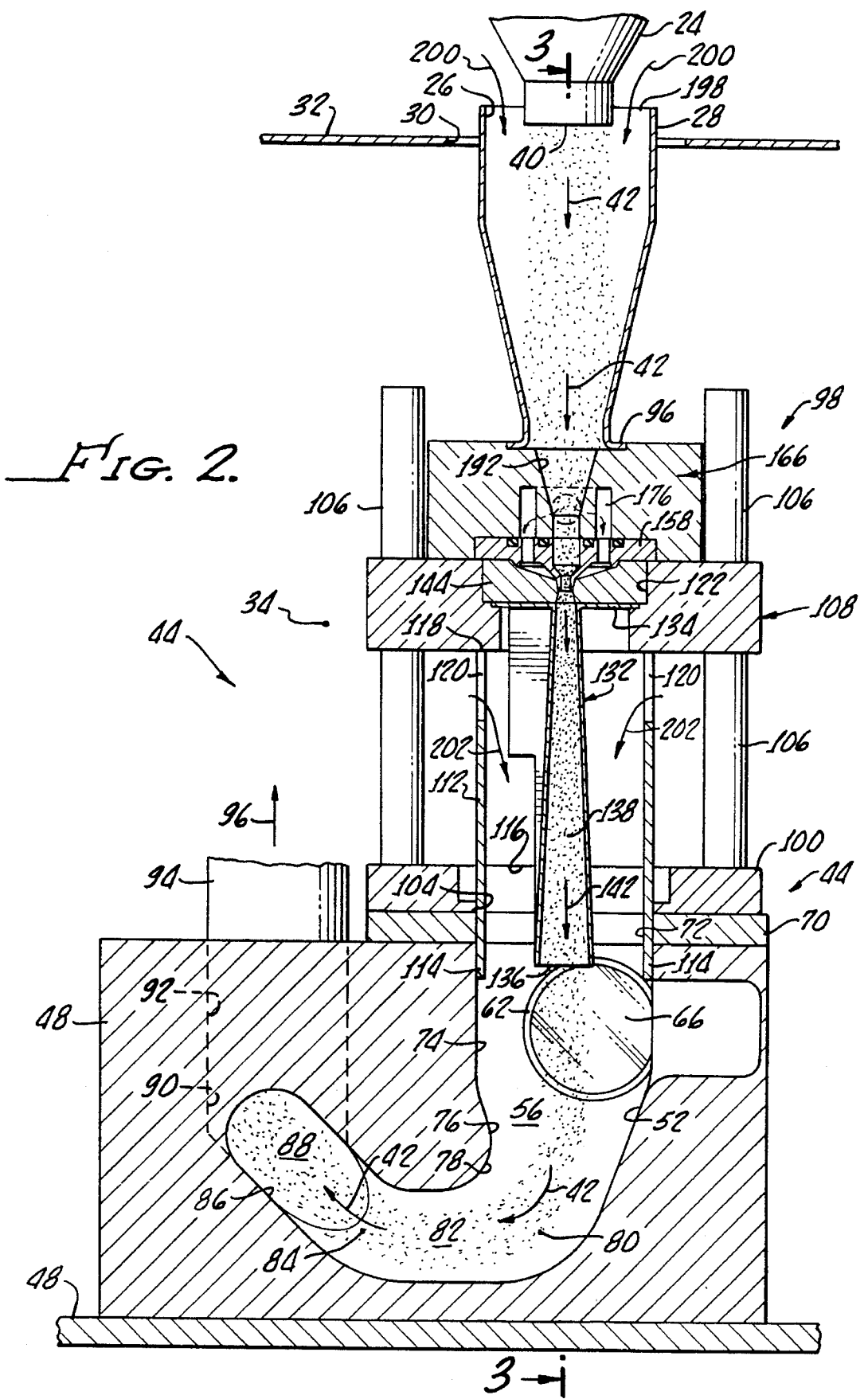
Figure 3:
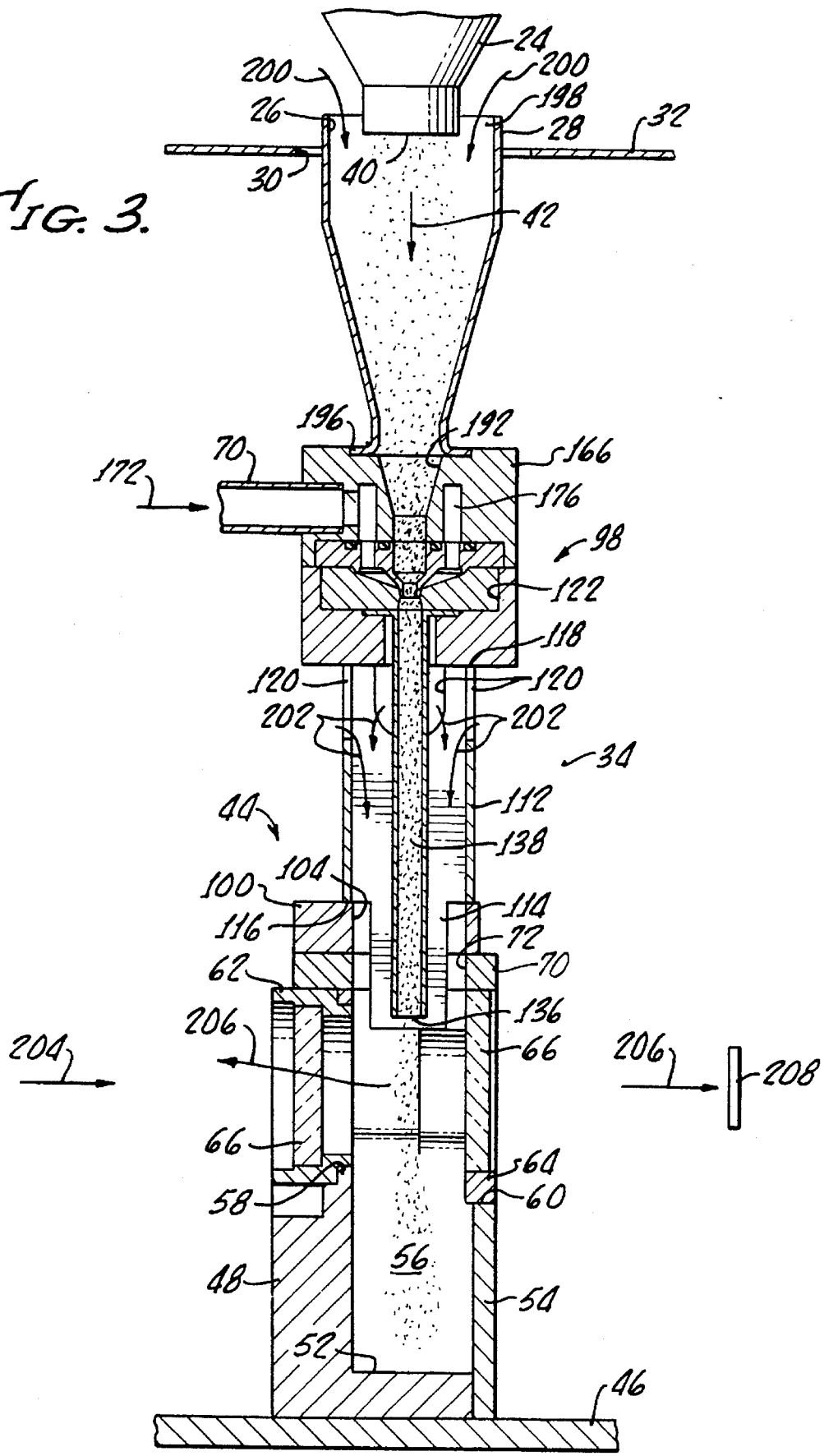
Figures 5, 6, 7:
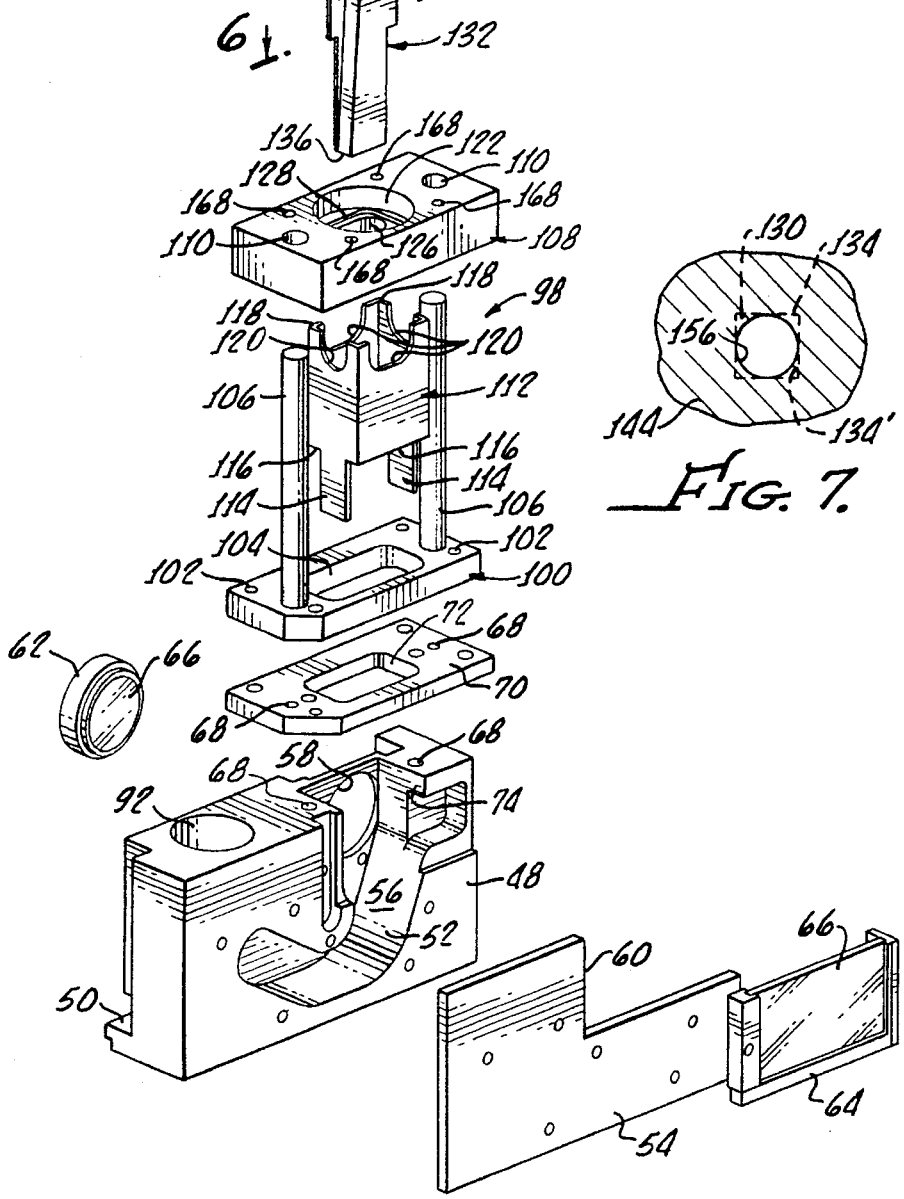

Viewing now FIGS. 2, 3, and 5 in conjunction, with particular attention to FIG. 2, is will be understood that the sample sieve cup 22 includes a sieve screen (not seen in the drawing Figures), above which is disposed a bulk sample of particulate material (also not seen in the drawing Figures), the particle size distribution of which is to be determined with analyzer 10. Sample sieve cup 22 is subjected to a vibratory motion imposed upon the cup clamp 20 through a supporting arm (not seen in the drawing Figures) which extends laterally into the chamber 18 from the left-hand part of the dry particle feeder 14, as seen in FIG. 1. Preferably, the vibratory motion imposed upon the sample sieve cup 22 is an orbital motion, and is oriented in a vertical plane, as depicted by arrow 38. The vertical orbital oscillation of the sample cup 22 is believed to be advantageous in terms of the avoidance of both audible and structural noise in the environment of the analyzer 10. Such noise could possibly interfere with or impair the delicate optical system used in diffraction analysis. Also, this type of orbital motion is believe to help avoid impaction and clumping of the particulate sample within the sample cup 22.

The vibratory motion imposed upon the sample cup 22 causes particles from the bulk sample to drizzle through the screen of this sample cup, and to be discharged from an open lower end 40 of the funnel portion 24 of the sample cup in the form of a drizzle or cloud of fine particulates, as is indicated by arrow 42. The applicant believes that the vertical orbital oscillation of the sample cup 22 results in the particles being drizzled therefrom at a monotonic rate as a function of oscillation rate. Consequently, control of the drizzle rate of the particles (arrow 42) from the sample cup is easier to achieve, is more predictable, and improved accuracy and repeatability of test results are obtained. Within the analysis cell well 34 of the particle analyzer 10, is disposed an analysis cell assembly, generally referenced by the numeral 44. This analysis cell assembly 44 includes the conduit member 28 which extends upwardly through the opening 30 of cover plate 32.

Analysis cell assembly 44 sits upon a floor 46 (seen in FIG. 2) of the well 34, and a base portion 48 of the analysis cell assembly 44 includes a projecting flange portion 50 (best seen in FIG. 5), by which the analysis cell assembly 44 may be clamped into position in a cell socket (not shown) on floor 46. Base portion 48 defines a generally U-shaped recess 52, and sealingly carries a closure plate 54 cooperating with the base portion 48 to bound a flow path portion 56 in the U-shaped recess, and which is described in greater detail below. Importantly, in order to provide windows for light passage through the analysis cell, the base portion 48 and closure plate 54 each define a respective one of a pair of aligned opposite apertures 58, 60. Respectively received sealingly at the apertures 58, 60 are one of a window carrier ring 62, and a window carrier frame 64. The ring 58, and frame 60 each sealingly include a transparent glazing material, generally referenced with the numeral 66. The glazing material in ring 62 is a round disk, while the material in frame 64 is of rectangular shape.

Carried upon the base portion 48 and secured sealingly thereto by fasteners (not seen in the drawing Figures, but holes for which are seen in FIG. 5, and are generally referenced with the numeral 68), is a plenum floor member 70. The plenum floor member 70 defines a downwardly extending through outlet opening 72, which is rectangular in plan view and which is also congruent with the adjacent end of the U-shaped recess 52. The recess 52 of base member 48 is U-shaped in plan view so that the flow path portion 56 is rectangular in plan view. A first vertically extending and cylindrical analysis-passage part 74 of the flow path portion 56 is congruent with the opening 72, and includes the windows 66 on opposite sides of this flow path portion. This portion 74 of the flow path 56 forms the analysis chamber for the cell assembly 44.

Almost immediately below the windows 66, the flow path portion 56 includes a convergent part, referenced with the numeral 76. This convergent flow passage part 76 leads smoothly to a throat part 78 which immediately (at 80) turns about 90 degrees to extend horizontally (as is referenced with numeral 82) a short distance adjacent to the lower extent of the base portion 48. After this short horizontal run 82, the throat part 78 again turns about 90 degrees (at 84) to extend upward a short distance. The throat part 78 then communicated via a window 86 to a flow path part 88. Flow path part 88 is defined by a vertically extending boring or passage 90, which opens upwardly on the base portion 48 in an opening 92, best seen in FIG. 5. The opening 92 is preferably slightly tapered outwardly so that the nozzle end of a conventional vacuum hose 94 (partially depicted in FIG. 2) will slip into and be frictionally retained within the bore passage 90. Vacuum hose 94 leads to a conventional industrial vacuum cleaner (not shown) with a fine filter element for insuring that the particles under test are not blown out into the ambient. Arrow 96 indicates the flow of air and particulates caused from the flow path 56 by the vacuum applied to hose 94. Consequently, it will be understood that the flow path 56 is maintained at a sub-ambient pressure, and that ambient air is drawn into the flow path 56 via openings therefrom to ambient.

Figure 4:
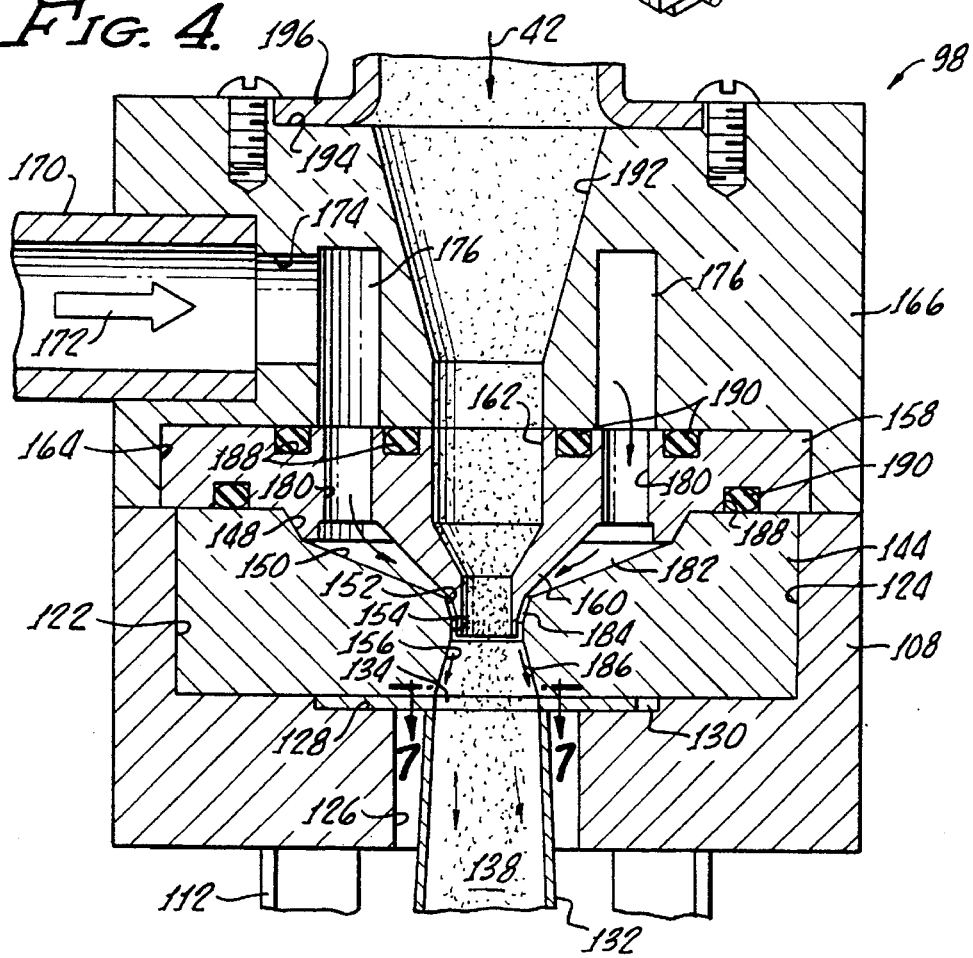

Still considering FIGS. 2, 3, and 5, and now also considering FIG. 4, it is seen that the analysis cell assembly 44 includes a de-agglomerator sub-assembly 98. This de-agglomerator sub-assembly also provides structural features and functions, as will be seen, for providing a columnated flow of ambient sheath air around and substantially matching the pressure and velocity of the cloud of particulates 42 as these particulates flow into the analysis chamber at portion 74 of the flow path 56. Viewing FIGS. 2 and 3 together for an overview of this de-agglomerator sub-assembly 98, it is seen that a base plate member 100 is secured to the floor member 70 by threaded fasteners (not seen in the drawing Figures). The holes 102 for accepting these fasteners can be seen in FIG. 5.

Base plate member 100 defines a rectangular through opening 104, which is generally congruent with and matching in shape to the opening 72 in the floor member 70. On each side of the opening 104, adjacent to the narrower ends thereof, the base plate member 100 carries a pair of spaced apart vertically extending parallel guide rods 106. These guide rods 106 slidably receive a manifold block 108, which is also generally rectangular, and defines a pair of spaced apart holes 110 for slidably receiving the rods 106 (viewing especially FIG. 5).

Captured between the base plate member 100 and manifold block 108 is a thin-walled tubular flow guide member 112, which is generally rectangular in plan view. The flow guide member 112 includes a pair of opposite tangs 114 which extend downwardly into the analysis chamber portion 74 of the cell assembly 44. The tangs 114 have a close fit in the openings 72 and 104 of the floor member 70 and base plate member 100, respectively. Also, the flow guide member 112 defines a lower edge surface 116 which rests sealingly upon the upper surface of the base plate member 100. At its upper edge surface 118, the flow guide member 112 supportingly engages the lower surface of the manifold block member 108. At each of the four sides of the flow guide member 112, this member defines a notch, each generally referenced with the numeral 120. As will be seen, these notches 120 communicate with and admit ambient air into the flow guide member 112, and into analysis cell chamber 74.

The manifold block member 108 defines a stepped through bore 122, which has an upper round portion 124, and a lower stepped oval portion 126. Received in the bore 122 on a shoulder 128 defined on the lower stepped oval portion 126 of the bore 122 is a flange portion 130 of a thin-walled expansion nozzle member 132. The expansion nozzle member 132 defines an upper opening 134, a lower opening 136, and an expanding flow path 138 extending between these openings. As is seen in FIGS. 2 and 3, the lower opening 136 of the expansion nozzle member 132 is disposed in the analysis chamber 74 immediately above the window members 66. FIG. 6 shows that the expansion nozzle member 132 is formed by overlapping and welding together two L-shaped thin sheet metal parts 140. The parts 140 each have a shorter leg 142 of constant dimension, so that the flow path 138 of expansion nozzle member 132 enlarges in one dimension only downwardly along the length of this nozzle member. The other dimension (parallel to the short legs of parts 140) remains substantially constant along the length of the nozzle member 132. The direction of expansion of the flow path 138 is parallel to the windows 66, and perpendicular to the sight line through chamber 74 through these windows.

Captured in the bore portion 124 of manifold block 198 is a nozzle block member 144, best seen by viewing FIGS. 4 and 5. This nozzle block member 144 defines a stepped and tapered through bore 146, which at its lower end communicates with the upper opening 134 of the expansion nozzle member 132. Particularly, the bore 146 of nozzle block member 144 includes an upper shallow tapering entrance portion 148 leading to a shallow more tapered convergent entrance portion 150. This entrance portion 150 leads to a steeply tapered convergent entrance portion 152, and thence to a cylindrical throat portion 154. The throat portion 154 leads to a divergent exit portion 156. As can be seen viewing FIG. 4, the exit portion 156 leads to the upper opening 134 of the nozzle member 132. Importantly, the bore 146 is circular in all of its parts, while the flow path 138 and the upper opening 134 are rectangular. As is seen in FIG. 7, the upper opening 134 to flow path 138 is substantially square. The lower opening of bore 146 (at the outlet of bore portion 156) is inscribed within the square opening 134. Consequently, four corner portions 134' of the opening 134 are disposed outwardly of the lower opening of the bore 146, and represent step-wise surface discontinuities in the profile of the surface presented to flow in a downward direction along these surfaces.

Atop the nozzle block member 144 is captured a nozzle ring member 158. This nozzle ring member 158 defines a downwardly protruding portion 160, and central stepped and tapered through bore 162 opening on this protruding portion 160. The protruding portion 160 extends downwardly into the throat portion 154 of the nozzle block member 144 with a radial clearance therefrom, as is best seen in FIG. 4. Capturing the nozzle ring member 158 in a recess 164 thereof is a manifold cap member 166. This manifold cap member 166 is secured to the manifold block member 108 by plural fasteners (not seen in the drawing Figures, but the holes 168 for which are visible in FIG. 5). The manifold cap member 166 receives connection from a conduit 170 conveying a controlled flow of pressurized air, as is indicated by the arrow 172, via a bore 174 into an annular chamber 176. Annular chamber 176 is defined by an annular counter bore 178 on the lower side of the cap member 166.

Nozzle ring member 158 defines plural circumferentially arrayed through passages 180 communicating the chamber 176 with an annular chamber 182 defined within the portions 148 and 150 of the bore 146 outwardly of the protruding portion 160 of the nozzle ring member 158. The chamber 182 is downwardly convergent and leads to a convergent annular radial nozzle gap, generally indicated with the numeral 184, which is defined outwardly of the protruding portion 158 and within the bore portions 152 and 154 of the nozzle block member 144. Consequently, a controlled flow of high velocity pressurized air, as is indicated by arrows 186 flows downwardly in the gap 184 to be discharged from this gap into the divergent bore portion 156 along the wall of this bore portion as a sheath of high velocity air attached to this wall by Coanda effect. The nozzle ring member 158 is provided with plural concentric grooves, generally indicated with the numeral 188, each of which receives an O-ring type of sealing member, generally indicated with the numeral 190, for sealingly containing the pressurized air admitted via conduit 170.

Viewing FIGS. 4 and 5, it is further seen that the manifold cap member 166 defines a stepped and tapering through bore 192, which at its lower end matches and communicates with the bore 162 of the nozzle ring member 158. At its upper extent, the bore 192 includes a shallow circular counterbore portion 194 receiving a flange part 196 of the conduit member 28.

Having considered the structure of the analysis cell assembly 44, attention may now be directed to the use of the particle analyzer 10. As was described above, the sample sieve cup 22 drizzles particles from the bulk sample into the upper end or mouth 26 of the conduit member 28, recalling arrow 42 representing a cloud of these particles falling by gravity in ambient air. Because the funnel portion 24 of the sample cup 22 is smaller than the mouth 26 of the conduit member 26, there is defined cooperatively therebetween a first sheath air inlet 198 receiving ambient air (as represented by arrows 200 viewing FIGS. 2 and 3) for flow as a first surrounding sheath air flow between the particle drizzle 42, and the walls of the conduit member 28, remembering that ambient air flow is caused by vacuum from the vacuum source hose 94 (recalling FIG. 2), and by aspirator effect caused by the discharge of pressurized air from the gap 184 (viewing FIG. 4). The particle drizzle and first sheath air travel together downwardly in the conduit member 28 and into the bore 192 of manifold cap member 166, viewing FIG. 4, with the convergent lower portion of the conduit 28 and the tapering portion of bore 192 an increase of the flow velocity of the particulates and air together. Gravitational influence on the drizzled particles is thought to possibly assist this particle acceleration, and the design of the analysis cell assembly 44 is such that opposition to gravitational force is not required at any point. The first sheath air flow keeps the particles from contacting or adhering to the walls of the conduit member 28, the inner surfaces of which are readily accessible and easy to clean should wall contamination occur.

Subsequently, the air flow and particles enter the bore 162 of nozzle ring 158, with the further tapering of this bore effecting a further increase in flow velocity. It is important to note that in the conduit member 28, manifold cap member 166, and nozzle ring member 158, the flow regime is bulk uniform laminar flow with the expected viscous boundary layer adjacent to the walls of the flow path being present, and having a progressively slower velocity with increasing closeness to the boundary walls. However, at the lower end of the annular radial nozzle gap 184 (that is, at the lower end of the protruding portion 160 of nozzle ring 158), the annular high velocity air flow 186 circumscribes the flow 42 of particulates and ambient air as a second sheath air flow. This high velocity air flow 186 has a speed much above that of the air flow 42, and attaches to the wall of bore 156 by Coanda effect. As a result, when the flow 42 exits downwardly from bore 162 into bore portion 156, a sudden change in flow regime with attendant high shear takes place, it is believed. This high shear effect is believed to be effective to break up many agglomerations of the particulates in the flow 42. Dependent upon the operating pressure present in the chamber 176, the flow 186 may be of sonic velocity, or of sonic velocity with under-expansion. When such sonic velocit air encounters the much slower moving air and particulates of the flow 42, a high shear results. If the air flow 186 is sonic with under-expansion, the air flow 186 will continue to expand toward ambient conditions after its exit from the gap 184. This expanding sonic air flow may experience local oblique shocks as it expands toward ambient pressure conditions, further adding to the deagglomerating action of the sub-assembly 98. In order to appreciate the velocity of the air flow 186, and the difference between the speed of this air flow and flow 42, the following table sets out the speeds of these flows as a function of the air pressure applied to conduit 170 (i.e., pressure in chamber 176):

TABLE

MEASURED VELOCITIES AT VARIOUS ORIFACE AIR PRESSURE SETTINGS

| Pressure in chamber 176 "PSI" | Second sheath air velocity 186 at gap 184 "ft/min" | Second sheath air velocity 186 at exit of bore 156 "ft/min" | Velocity differential second sheath air flow to sample flow 42 "ft/min" | Velocity sample in "ft/min" |
|---|---|---|---|---|
| 10 | 56184.11 | 19532.24 | 36651.86 | 2300 |
| 15 | 61788.32 | 25344.98 | 36443.34 | 2900 |
| 20 | 61788.32 | 27425.50 | 34362.82 | 3100 |
| 25 | 61788.32 | 30735.18 | 31053.14 | 3400 |
| 30 | 61788.32 | 33104.11 | 28684.21 | 3600 |
| 35 | 61788.32 | 35646.27 | 26142.0 | 3800 |
| 40 | 61788.32 | 38420.41 | 23367.90 | 4000 |
| 45 | 61788.32 | 41524.39 | 20263.93 | 4200 |
| 50 | 61788.32 | 45145.73 | 16642.59 | 4400 |

Subsequently, the flow 42 is subjected to an interval of high shear extending from the exit of bore 162 at least to the upper surface of flange 130, recalling FIGS. 4 and 7. At the flange 130, a portion of the high velocity second sheath air flow 186 from the nozzle gap 184 transitions to the corner areas 134' of the diffuser 132, as seen in FIG. 7, recalling that the flow 186 is wall-adhered by Coanda effect. As a result, an additional increase in the turbulence of the combined flow (now referred to as flow 42/186) occurs, it is believed. The combined flow 42/186 is believed to enter the flow path 138 of the expansion nozzle member 132 in a highly turbulent condition, so that this turbulence is effective to further break up agglomerations of the particulates. This combined flow 42/186, which becomes an admixture of the second sheath air flow and the first sheath air flow, continues downwardly in the expansion nozzle member 132, diffusing to a lower velocity with increasing area of this nozzle flow path 138. At the lower end 136 of the flow path 138, the combined flow 42/186 exits the expansion nozzle member 132 into the analysis cell 74 as a substantially columnar flow of particles in air, which columnar flow is rectangular in cross section, recalling FIG. 6. This rectangular flow of particles has a major dimension transverse to the sight line through the analysis cell 74.

Also delivered into the analysis chamber 74 is a descending column of third sheath air 202 from the interior of flow guide member 112, around expansion nozzle 132. This flow of third sheath air is provided via notches 120 as a result of the vacuum applied to the flow path 56 by the vacuum hose 94. Importantly, the velocity of flow of third sheath air 202 is preferably matched to that of the combined flow 42/186 so that there is little or no velocity difference between these flows as they pass together simultaneously downwardly and though the analysis chamber 74 of analysis cell assembly 44 between the windows 66.

In the analysis chamber 74 of the analysis cell assembly 44, beamed light or other electromagnetic radiation (represented by arrow 204, viewing FIG. 3, and all referred to collectively herein as, "optical interrogation beams") is directed through one of the windows (66). Forward and back scattered light, as well as obscuration and diffraction information from the columnated particulates 42 is represented by arrows 206, and is incident on receptors 208 for further analysis in conventional ways. Subsequent to the analysis chamber 74, the particles 42 are drawn through the remainder of the flow path 56, and out vacuum hose 94. Because the particles are deeply sheathed in the second sheathing air flow as they pass through the flow path 56 they do not generally impact on, adhere to, or settle out on the walls of the analysis cell assembly 44. However, should some particles ever remain in the analysis cell assembly 44, any wall contamination will occur below the analysis chamber 74 and, therefore, will not affect subsequent measurements. Moreover, this assembly 44 is easily disassembled and cleaned, and its resulting cleanliness can be visually verified (i.e., by removal of cover plate 54).

Consideration of the above description of the disclosed preferred embodiment will reveal that the particles are drizzled straight downwardly from their bulk sample into the analysis passage. The design of the analysis cell does not fight or try to avoid the effect of gravitational influence on the particles, but instead uses this force to advantage. It follows that particle dropout is simply not a problem from which the Applicants' invention could suffer. Also, the conduit member 28 and base portion 48 with U-shaped flow path 56 cooperatively define a particle flow path which is generally of J-shape. That is, the conduit member 28 and de-agglomerator assembly 98 forms the upper reach of the J-shape, while the U-shaped flow path 56 completes the lower hook of the J-shape. The resulting analysis cell assembly is small and can be inserted into the analysis well 34 of a conventional particle analyzer 10 previously used for testing liquid-borne particulates. The columnated drizzling particles are not perturbed or baffled or turned from their downward course until after they have passed the windows 66 of the analysis chamber 74 and have been interrogated by the beam 204. Also, the de-agglomerator assembly 98 is effective to break up agglomerations of particulates down to a size of less than one micron. That is, particulates down to about 0.6 microns can be obtained by attrition of agglomerations which conventionally would have been seen as single particles. This attrition of agglomerations of particulates is achieved without impacts or other effects fracturing or breaking the particles themselves, so that "fines" are not created in the flow of particulates by the very apparatus with which it is hoped to obtain an analysis of the particulate sample in its original condition. Thus, the accuracy of the presently disclosed dry particle analysis cell is thought to be without equal heretofore.

While the present invention has been depicted, described, and defined by reference to a particular preferred embodiment of the invention, such reference does not imply a limitation on the invention, and no such limitation is to be inferred. Only the spirit and full scope of the appended claims is intended as a limitation on the invention. Further, the invention is subject to modifications and variations which will suggest themselves to those skilled in the pertinent art. Such modifications and variations are intended to fall within the scope of the appended claims.

We claim:

1. A dry particle analyzer comprising: means for drizzling particles from a bulk sample thereof, means for providing a downward flow of first sheath ambient air around said drizzling particles in a flow regime of laminar bulk flow with a surrounding viscous boundary layer, means for suddenly changing the flow regime of said drizzling particles and first sheath air to a flow regime with a surrounding second sheath of high velocity air causing high shear and acceleration of said drizzling particles and first sheath air flow and with admixture of said second sheath air, means for columnating and decelerating said particles and said admixture of first sheath air and second sheath air, means for providing a downward and columnar flow of third sheath ambient air around said columnated drizzled particles and first and second air flows admixed together and substantially in velocity union therewith, and means defining a vertically downwardly extending optical analysis cell passage receiving the unified downward flow of drizzled particles and admixed first and second sheath air surrounded by said third sheath air for columnated downward flow therein, whereby the drizzled particles flow downwardly continuously from said bulk sample and through said analysis cell passage.

2. The dry particle analyzer of claim 1 wherein said means for providing a downward flow of first sheath ambient air around said drizzling particles in a flow regime of laminar bulk flow with a surrounding viscous boundary layer includes a sieve cup providing a downward gravitational drizzle of particles in response to agitation thereof, and a conduit receiving said downward gravitational drizzle of the particles along with a surrounding flow of ambient air as said first sheath air flow.

3. The dry particle analyzer of claim 2 further including means for creating a sub-ambient pressure within said conduit to induce said surrounding flow of ambient air into said conduit in surrounding relationship with said drizzle of particles.

4. The dry particle analyzer of claim 3 wherein said means for creating a sub-ambient pressure includes a vacuum source communicating with said conduit.

5. The dry particle analyzer of claim 3 wherein said means for creating a sub-ambient pressure includes an aspirator receiving pressurized air and ejecting this pressurized air in a direction along the length of said conduit to provide said sub-ambient pressure therein.

6. The dry particle analyzer of claim 2 further including means for agitating said sieve cup, said means for agitating said sieve cup imposing a vertical orbital oscillation on said sieve cup.

7. The dry particle analyzer of claim 1 wherein said means for suddenly changing the flow regime of said drizzling particles and first sheath air to a flow regime with a surrounding second sheath of high velocity air causing high shear and acceleration of said drizzling particles and first sheath air flow and with admixture of said second sheath air includes an aspirator receiving pressurized air and providing an opening through which said drizzling particles and first sheath air is received, said aspirator defining an annular radial gap in surrounding relationship with said opening and said drizzling particles and first sheath air flow and from which said pressurized air is discharged axially along a length of said conduit.

8. The dry particle analyzer of claim 1 wherein said means for columnating and decelerating said particles and said admixture of first sheath air and second sheath air includes a divergent nozzle member receiving said drizzle of particles and first sheath air flow along with said high velocity air of said second sheath air flow, said divergent nozzle member diffusing said first and second air flows to a lower velocity and discharging said drizzled particles and said first and second air flows columnated into said downwardly extending optical analysis cell passage.

9. The dry particle analyzer of claim 8 wherein said divergent nozzle member defines an outlet which is of substantially rectangular shape in cross section, said nozzle member outlet having a major dimension which is perpendicular to an optical interrogation axis through said optical analysis cell passage, and discharging said drizzled particles and said first and second air flows together in a curtain of generally rectangular shape across said optical interrogation axis.

10. The dry particle analyzer of claim 8 wherein said divergent nozzle member further defines a step-wise discontinuity in the surface profile presented for bounding said high velocity said second sheath air flow, thereby to provide additional turbulence in said drizzle of particles and first sheath air flow along with said high velocity air of said second sheath air flow upon said nozzle member receiving said air flows.

11. The dry particle analyzer of claim 1 wherein said means for providing a downward and columnar flow of third sheath ambient air around said columnated drizzled particles and first and second air flows admixed together and substantially in velocity union therewith includes a flow guide member surrounding said columnated drizzled particles and first and second air flows admixed together and separated therefrom, said flow guide member including an opening receiving ambient air, and downwardly opening to said optical analysis cell passage.

12. The dry particle analyzer of claim 1 wherein said means defining a vertically downwardly extending optical analysis cell passage receiving the unified downward flow of drizzled particles and admixed first and second sheath air surrounded by said third sheath air for columnated downward flow therein includes a base member defining a generally J-shaped passage, said J-shaped passage having a descending leg which in an upper portion there of defines said optical analysis cell passage.

13. The dry particle analyzer of claim 12 wherein said J-shaped passage includes a convergent-divergent venturi nozzle shape.

14. The dry particle analyzer of claim 13 wherein said J-shaped passage further includes a divergent pressure-recovery section leading to an exit port.

15. The dry particle analyzer of claim 12 including said base member defining therein said analysis cell passage and said carrying opposed transparent windows bounding said analysis cell passage and providing for optical interrogation of said drizzled particles.

16. A dry particle analyzer apparatus comprising: means for providing a cloud of drizzled particles gravitationally descending in a relatively low-velocity laminar bulk flow of surrounding ambient first sheath air with a surrounding low-velocity viscous boundary layer, and a de-agglomerator for affecting attrition of agglomerations of said particulates, said de-agglomerator including:

a Coanda type aspirator defining an opening through which said bulk flow of drizzled particles and first sheath ambient air is received, said aspirator receiving pressurized air and defining an annular radial gap surrounding said opening and from which a high-velocity second sheath air flow is discharged axially of said opening, thereby to apply a sudden high air flow shear to said particles and first sheath air flow.

17. The dry particle analyzer of claim 16 wherein said de-agglomerator further includes a step-wise boundary surface profile change spaced downstream of said annular radial gap with respect to said second sheath air flow, said second sheath air flow traversing said step-wise boundary surface change to impose additional turbulence on said drizzled particles and first sheath air flow.

18. The dry particle analyzer of claim 17 wherein said de-agglomerator further includes a divergent nozzle member receiving said drizzled particles and first sheath air flow along with said second sheath air flow subsequent to said step-wise boundary surface change.

19. The dry particle analyzer of claim 18 wherein said divergent nozzle member defines corners providing said step-wise boundary surface profile change.

20. The dry particle analyzer of claim 18 wherein said divergent nozzle member defines an inlet opening, and a plurality of corners circumscribing said inlet opening to provide a like plurality of step-wise boundary surface profile changes, one profile change at each corner.

21. A method of de-agglomerating particles for optical dry particle analysis, said method comprising steps of:

drizzling particles from a bulk sample thereof;

providing a downward flow of first sheath ambient air around said drizzling particles in a flow regime of laminar bulk flow with a surrounding viscous boundary layer;

suddenly changing the flow regime of said drizzling particles and first sheath air to a flow regime with a surrounding second sheath of high velocity air;

using said second sheath of high velocity air to cause high shear and acceleration of said drizzling particles and first sheath air flow;

effecting admixture of said second sheath air with said first sheath air;

columnating and decelerating said particles and said admixture of first sheath air and second sheath air;

providing a downward and columnar flow of third sheath ambient air around said columnated drizzled particles and admixed first and second sheath air flows and substantially in velocity union therewith; and receiving the unified downward flow of drizzled particles and admixed first and second sheath air surrounded by said third sheath air into a vertically downwardly extending optical analysis cell passage for columnated downward flow therein.

22. The method of claim 21 further including the step of imparting high turbulence to said drizzled flow of particles and first and second sheath air flows before decelerating said admixed first and second sheath air flows.

* * * * *